(12) United States Patent
Reich

(10) Patent No.: US 6,811,973 B1
(45) Date of Patent: Nov. 2, 2004

(54) METHODS OF USING LABELED PROBE MOLECULES TO QUANTIFY TARGET MOLECULES

(75) Inventor: Norbert Reich, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/721,550

(22) Filed: Nov. 22, 2000

Related U.S. Application Data

(60) Provisional application No. 60/167,421, filed on Nov. 24, 1999.

(51) Int. Cl.[7] .............. C12Q 1/68; C12M 1/00; G01N 15/06; C07H 21/04
(52) U.S. Cl. ............ 435/6; 435/283.1; 435/287.1; 435/287.2; 435/288.3; 435/288.7; 436/501; 422/50; 422/68.1; 536/23.1; 536/24.1; 536/24.3; 536/24.31; 536/24.32; 536/24.33
(58) Field of Search ........... 435/6, 283.1, 287.1, 435/287.2, 288.3, 288.7, 289.1, 299.1, 305.1; 422/50, 68.1; 436/501; 536/23.1, 24.1, 24.3, 24.31, 24.32, 24.33, 22.1

(56) References Cited

U.S. PATENT DOCUMENTS

| | | | |
|---|---|---|---|
| 5,436,327 A | | 7/1995 | Southern et al. |
| 5,445,934 A | | 8/1995 | Fodor et al. |
| 5,512,439 A | * | 4/1996 | Hornes et al. ............ 435/6 |
| 5,525,711 A | | 6/1996 | Hawkins et al. |
| 5,652,099 A | * | 7/1997 | Conrad ..................... 435/6 |
| 5,723,591 A | | 3/1998 | Livak et al. |
| 5,744,305 A | | 4/1998 | Fodor et al. |
| 5,753,516 A | * | 5/1998 | Heagy et al. ........... 436/501 |
| 5,763,167 A | | 6/1998 | Conrad |
| 5,776,711 A | * | 7/1998 | Vyas et al. .............. 435/7.25 |
| 5,800,992 A | * | 9/1998 | Fodor et al. ............. 435/6 |
| 5,804,375 A | * | 9/1998 | Gelfland et al. ......... 435/6 |
| 5,807,525 A | | 9/1998 | Allen et al. |
| 5,846,729 A | * | 12/1998 | Wu et al. ................. 435/6 |
| 5,876,390 A | | 3/1999 | Hall et al. |
| 5,876,930 A | | 3/1999 | Livak et al. |
| 5,925,517 A | | 7/1999 | Tyagi et al. |
| 5,925,525 A | | 7/1999 | Fodor et al. |
| 6,001,571 A | * | 12/1999 | Mandecki ................ 435/6 |
| 6,100,030 A | * | 8/2000 | McCasky Feazel ....... 435/6 |
| 6,103,476 A | | 8/2000 | Tyagi et al. |
| 6,156,501 A | * | 12/2000 | McGall et al. ........... 435/6 |
| 6,187,530 B1 | * | 2/2001 | Scholin et al. ........... 435/4 |
| 6,312,906 B1 | | 11/2001 | Cass et al. |
| 6,451,530 B1 | * | 9/2002 | Hawkins ................. 435/6 |
| 6,485,903 B1 | | 11/2002 | Mayrand |
| 6,492,121 B2 | | 12/2002 | Kurane et al. |
| 6,495,326 B2 | * | 12/2002 | Kurane et al. ........... 435/6 |

FOREIGN PATENT DOCUMENTS

| | | |
|---|---|---|
| EP | 0 742 287 A2 | 11/1996 |
| WO | WO 95/31469 | 11/1995 |

OTHER PUBLICATIONS

Egholm et al "PNA hybridized to comlementary oligonucleotides obeying the Watson–Crick hydrogen bonding rules" Nature, Oct. 7, 1993, 365: 566–568.*

Allan, Barrett W. and Reich, Norbert O.; "Targeted Base Stacking Disruption by the EcoRi DNA Methyltransferase"; *American Chemical Society*; 1996; pp. 14757–14762 + figure.

* cited by examiner

*Primary Examiner*—BJ Forman
(74) *Attorney, Agent, or Firm*—Greenberg Traurig, LLP; Charles Berman, Esq.

(57) ABSTRACT

An assay system using labeled probe molecules to identify and quantify target molecules in a sample is disclosed. Where labeled probe molecules are present on a substrate such as a microarray, the identification of multiple different target molecules may be examined simultaneously. Alternatively, a known number of like probe molecules may be present on a substrate and a single target molecule may be quantified in a sample. Preferred labeled probe molecules are comprised fluorescent single stranded nucleotide analogs whose fluorescence is quenched by pairing with a homologous nucleotide target sequence.

19 Claims, 1 Drawing Sheet

Adenosine

Guanosine or
Inosine

Cytidine

Thymidine
or Uridine

METHODS OF USING LABELED PROBE MOLECULES TO QUANTIFY TARGET MOLECULES

CROSS-REFERENCE TO RELATED OF APPLICATIONS

This application claims the benefit of the prior filing date of U.S. provisional patent application No. 60/167,421, filed Nov. 24, 1999 and entitled "Polymer Array on a Solid Substrate".

FIELD OF THE INVENTION

This invention relates generally to array based assays and more particularly to microarrays or beads having labeled probes molecules which are designed to assist in the identification and quantification of target molecules including native molecules or mutant molecules.

BACKGROUND OF THE INVENTION

Currently, scientists are interested in examining the effect of different treatments or conditions on the human body. One method of exploring these effects is to examine the changes that occur in the expression or function of molecules within individual cells or tissues which are exposed to the treatments or conditions. The molecules which are effected by such exposure may then be qualitatively or quantitatively compared to the native molecules to examine the effect of the treatment or condition.

In determining the expression or function of any molecule, traditional methods in molecular biology are only useful at examining the effect of one agent on one cellular molecule, in one experiment, which means that any effect of on any given molecule, in general, is slow, expensive and difficult to assess. The advent of microarray technology has allowed scientists to examine the effect of one treatment or condition or combination of thereof on thousands of molecules simultaneously.

Microarray technology consists, generally, of probe molecules being attached to a solid substrate and target molecules, obtained from the exposed cells contacting the probe molecules. Typically, target molecules are labeled prior to exposure to the microarray. Once exposed to the microarray, some target molecules selectively form probe/target pairs by binding/hybridizing with the complimentary probe molecules on the microarray. The target molecules that do not form pairs are removed from the microarray. Where the probe/target pairs are formed on the microarray, the scientist can then visualize the probe molecules which were bound by labeled target molecules. The relative amount of probe/target pairs which form can be compared between groups of cells which are exposed to different treatments and cells which are not (controls) to determine the effect of the treatment. For example, the levels of expression of mRNA or protein as a target molecule may have changed, or alternatively, the conformation of a protein or carbohydrate may have changed. As thousands of molecules can be screened simultaneously using this technology, microarrys may be used to improve timeliness, effectiveness, accuracy and overall benefit-to-cost ratio for examining changes in molecular expression and function relative to traditional methods.

One difficulty in microarray technology thus far, however, has been the ability of scientists to efficiently and effectively identify and quantify the probe/target pairs which form on the microarray. As above, the target molecule is typically labeled, and that label is detected to identify the probe/target pair. However, the label may not be present on the target molecule in sufficient amounts to be detectable. If a target sequence is not adequately labeled, false negative results are obtained, meaning that probe/target pairs are formed, but not identified by the scientist. Labeling inadequacies often occur due to enzymatic reproducibility, inhibition and or incomplete incorporation of dyes.

SUMMARY OF THE INVENTION

Labeled probe molecules are disclosed where the label is detectable when the probe molecule is not paired with a complimentary target molecule, and the label is undetectable when paired with a target molecule. Such a system allows for a means of identifying target molecules in a sample without encountering the difficulty of labeling target molecules.

The probe and target molecules can be polymers of nucleic acids, amino acids or carbohydrates. The label is preferably fluorescent, and can be detected by those methods currently known or to be developed in the art, such as flow cytometry. The probe molecules can be attached to a solid substrate such as a microarray or a bead.

In one embodiment, the probe molecules are single-stranded, fluorescently labeled nucleotide sequence which are attached to a microarray. The fluorescing nucleotide probe molecule is quenched when hybridized to a complimentary target nucleotide sequence.

In an alternate embodiment, the probe molecules are single-stranded, fluorescently labeled oligonucleotide sequences comprised in part or entirely by nucleotide base analogs.

Such a system also allows for a means of quantifying target molecules in a sample. In an alternate embodiment, a known number of labeled probe molecules are attached to a bead which can be contacted with the target sequences within a cellular sample. When probe/target pairs are formed, the fluorescence of the probe molecule will be decreased. When a number of probe/target pairs are formed which is substantially equal to the number of probe molecules present on the head, the fluorescence of the probe molecule will be substantially eliminated. Thus, the beads can be used to quantify the amount of a target molecule in a cellular sample.

The above described and many other features and attendant advantages of the present invention will become apparent from a consideration of the following detailed description when considered in conjunction with the accompanying drawings.

BRIEF DESCRIPTION OF THE DRAWINGS

Detailed description of the embodiments of the invention will be made with reference to the accompanying drawings.

DETAILED DESCRIPTION OF THE INVENTION

Figure 1A:
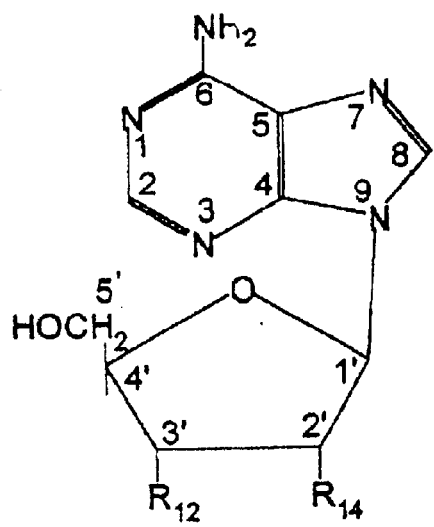
FIG. 1 shows the known structures for native adenosine (1A); guanine and inosine via a generic structure (1B); cytidine (1C); and thymidine and uridine via a generic structure (1D).
Figure 1B:
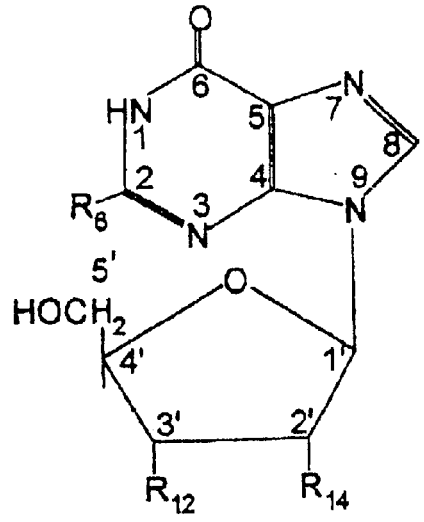
Figure 1C:
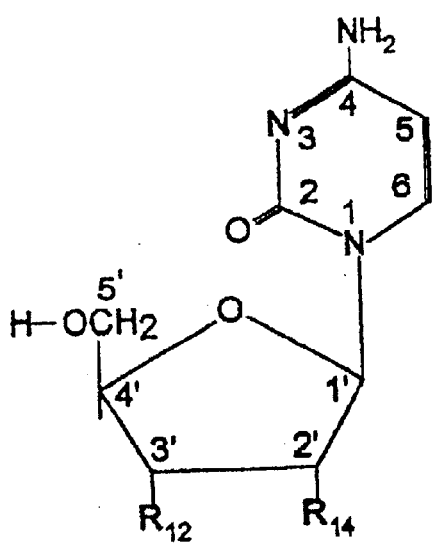
Figure 1D:
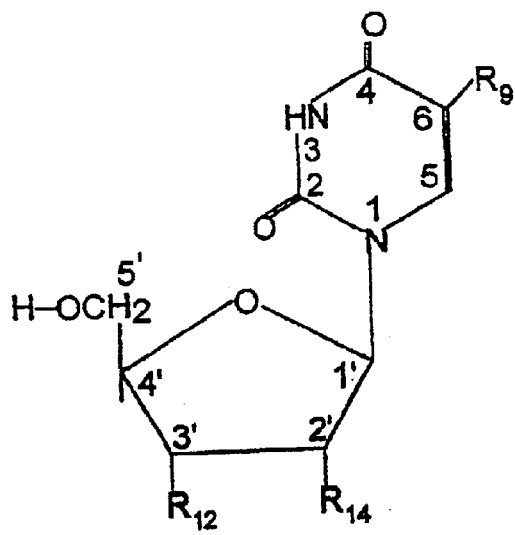

This description is not to be taken in a limiting sense, but is made merely for the purpose of illustrating the general principles of the invention. The section titles and overall organization of the present detailed description are for the purpose of convenience only and are not intended to limit the present invention.

Probe Molecules

The invention utilizes labeled probe molecules wherein the label is detectable when the probe molecule is not paired with a complimentary target molecule, and the label is undetectable when paired with a target molecule. As mentioned, this invention allows for a means of identifying and quantifying a target molecule in a cellular sample without encountering the difficulty of labeling target molecules.

The probe and target molecules can be polymers of nucleic acids, amino acids or carbohydrates, and complimentary pairs may form due to hybridization, annealing, or binding, for example between any of a nucleic acid, amino acid or carbohydrate polymer. The probe and target molecules can be synthesized or extracted from an organic source.

Where the probe molecules are nucleic acids the molecules may be single stranded or double stranded. Where the probe molecules are nucleic acids, the polymers may be comprised of native nucleotide bases (adenosine, guanine/inosine, cytidine or thymidine/uridine) or of nucleotide analogs, or any combination thereof. Further, the probe molecules can be comprised of a variety of different nucleotide analogues with preferred analogues having substantially the same or higher hybridization affinity for a target sequence as does a probe molecule comprised of native bases of the same length. More preferably the probe molecules are comprised of nucleotide analogues which can substitute for a native nucleic acid bases in all or any of enzymatic reactions involving (1) nucleic acid replication; (2) ligation and (3) phosphorylation.

Nucleotide analogs including heterocyclic pyrimidine or purine structural analogs of naturally occurring bases which are fluorescent under physiological conditions may be used. Examples of other nucleotide analogues which may be useful in this invention include, but are not limited to: 2-amino purine at least for adenosine or guanine; ribonucleoside or 2,6-diamino ribonucleoside, formycin A, formycin B, oxyformycin-B, toyocamycin, sangivamycin, pseudoouridine, showdomycin, minimycin, pyrazomycin, 5-amino-formycin A, 5-amino-formycin B or 5-oxo-formycin A at least for adenosine; 4-amino-pyrazolo [3,4d] pyrimidine, 4,6-diamino-pyrazolo [3,4d] pyrimidine, 4-amino-6-oxo-pyrazolo [3,4d] pyrimidine, 4-oxo-pyrazolo [3,4d] pyrimidine, 4-oxo-6-amino-pyrazolo [3,4d] pyrimidine, 4,6-dioxo-pyrazolo [3,4d] pyrimidine, pyrazolo [3,4d] pyrimidine, 6-amino-pyrazolo [3,4d] pyrimidine or 6-oxo-pyrazolo [3,4d] pyrimidine at least for cytosine or thymidine.

Finally, the probe molecule can be comprised of native nucleotide bases or nucleotide analogs, some of which or all of which are labeled. Preferably, some or all of the nucleotides are labeled with a fluorescing label. For example, in some embodiments only one base e.g. adenosine is substituted with an analogue (such as formycin, 2-amino purine, ribonucleoside or 2,6-diamino ribunucleoside), while the other nucleotides in the sequence are native. In other embodiments all the purines or alternatively all the pyrimidines are changed from the native nucleotide to a fluorescent nucleotide analog.

Those skilled in the art reading this disclosure will recognize that various types of different fluorescent nucleotides or analogues can be used in connection with the present invention. Specific examples are provided above, and others are described in U.S. Pat. No. 5,763,167 to Conrad; U.S. Pat. No. 5,925,517 to Tyagi, et al.; U.S. Pat. No. 5,876,930 and U.S. Pat. No. 5,723,591 to Livak, et al.; U.S. Pat. No. 5,525,711 and WO 95/31469 issued to Hawkins, et al. all of which are incorporated herein by reference in their entirety.

Alternatively, the nucleic acid based probe molecule can be labeled after the probe molecule is produced. Detectable labels can be attached by a variety of known procedures. Standard labeling protocols for amino acids and nucleic acids are described, for example in Sambrook et al.(1989) *Molecular Cloning*: A Laboratory Manual, 2$^{nd}$ Ed. Cold Spring Harbor Laboratory, Cold Spring Harbor, N.Y.; Kambara, H. et al. (1988) *Biotechnology* 6:816–821; Smith, L. et al., (1985) *Nuc. Acids Res.* 13:2399–2412; for polypeptides, see, e.g., Allen, G. (1989) *Sequencing of proteins and Peptides*, Elsevier, N.Y., and Greenstein and Winitz (1961) *Chemistry of the Amino Acids*, Wiley and Sons, New York. Carbohydrate labeling is described, for example in Chaplin and Kennedy (1986) *Carbohydrate Analysis: A Practical Approach*, IRL Press, Oxford—see also U.S. Pat. No. 5,652,099 issued to Conrad, all of which publications are incorporated herein by reference in their entirety.

The fluorescing label is preferably 2-aminopurine, which fluoresces at a range of about 300 nm to about 700 nm, most preferably, the fluorescence is detectable by the unaided human eye. The label may be fluorescent, and can be detected by those methods currently known or to be developed in the art, such as flow cytometry. Further, the label preferably fluoresces at a wavelength that is visible to an unaided human eye. Methodology utilizing 2-aminopurine as a labeled molecules is disclosed in Allen and Reich *Biochemistry* 1996, 35:1457–14762, herein incorporated in its entirety.

The probe molecules comprised of nucleotides can be produced using the known technology use to produce oligonucleotides, cDNA or RNA sequences. The probe molecules using nucleotides may have a sugar-phosphate backbone which is identical to that of a native molecule. However, in some embodiments it can be desirable to provide a modified backbone to enhance nuclease resistance, for example, which can enhance the reusability of the microarrays. Techniques for modifying backbones are described in at least European Application EP 0 742 287 A2 to McGall, et al., incorporated herein by reference in its entirety.

The probes molecules comprised of nucleic acids can be of any desired length, but are preferably longer than four bases or analogs long, and most preferably about 6 to about 300 or more nucleotides.

As those skilled in the are will recognize, probe molecules may also be amino acid based or carbohydrate based; such polymers can be synthesized and labeled according to methods of those presently known or to be developed by those skilled in the art, and those cited above.

Solid Substrates

Microarrays

Microarrays useful in this invention are any substrates which maximally facilitate the attachment of probe molecules thereto, and minimally interfere with probe/target pairing and further minimally interfere with detection of the label on the probe molecules.

In one embodiment, the microarray has probe molecules of different molecules attached to its surface. In an alternate embodiment, the surface of the microarray is divided into quadrants, each quadrant having a different probe molecule sequences. Preferably, all of the probe molecules in any quadrant are substantially similar in sequence (such as greater than 85% homologous), and preferably each different quadrant contains a different probe molecule sequence or a different quantity of any probe molecule sequence. However, in some embodiments, each quadrant may have more than one probe molecule sequence.

The microarrays of the present invention may have varying number of quadrants, or distinct sub-areas of the microarray. The microarrays preferably can include from about 10 to about 10,000 or more quadrants. Each quadrant preferably has a surface area of 1 square centimeter or less. The quadrant density of the microarray, or the number of quadrants per square centimeter of microarray surface area, may vary. Probe densities may be from about 100 copies to about 10,000 copies of a probe molecule per quadrant. Probe densities as high as 400 or more oligonucleotides per $cm^2$ have been described in U.S. Pat. No. 5,744,305 to Fodor, et al., and probe densities of as high as 1,000 or more nucleotides per $cm^2$ have been described in U.S. Pat. No. 5,445,934 issued to Fodor, et al., both patents are hereby incorporated by reference in their entirety.

Microarrays may be produced by synthesizing polymers thereon as is disclosed in U.S. Pat. No. 5,436,327 to Southern, et al. (arrays with fluorescent nucleotide analogues) or U.S. Pat. Nos. 5,445,934 and 5,800,992 to issued to Fodor, et al.(single stranded oligonucleotide probe molecules on the microarray surfaces), herein incorporated by reference.

In some embodiments, where probe molecules exceed about 200 molecules, for example, it is preferable to synthesize the probe molecules separately, and then attach them to the substrate. This method is disclosed in U.S. Pat. No. 5,807,525 to Allen, et al., herein incorporated by reference in its entirety. One advantage of the later method of making the microarray is that microarrays may have a higher purity of the desired sequences and, facilitate the production of sequences of any desired length or varying lengths.

Beads

Beads useful in this invention are any substrates which maximally facilitate the attachment of probe molecules thereto, and minimally interfere with probe/target pairing and further minimally interfere with detection of the label on the probe molecules.

In some embodiments, beads are comprised of a ferromagnetic metal coated with a non-soluble polymer material, and the polymer has, coated on its surface, the probe molecules.

Beads can be produced in any size and are preferably less than 20 $\mu$m in diameter, and more preferably less than 10 $\mu$m in diameter.

In one embodiment, the beads have probe molecules of the same sequence attached to its surface. Preferably, the quantity or number of probe molecules attached to the bead are known. Preferably, each bead has about 100 to about 1,000 or more probe molecules. A variety of beads can be produced and each bead having the same or a different number of probe molecules attached to its surface. Alternatively, in some embodiments, each bead may have more than one probe molecule sequence attached thereto or have an unknown quantity of probe molecules.

Method of Identifying Changes in Target Molecule Expression or Function

In one method of using the invention, the presence of a target molecule (or the ability of a target molecule to bind a probe molecule) within a sample can be determined by comparing the level at which the label is detected in any quadrant before and after being exposed to the target molecules in the sample. For example, a microarray having labeled probe molecules attached in distinct in quadrants can be evaluated by detecting the level of label expressed within each quadrant a first time. Then, a sample having unlabeled nucleotide target sequences can be added to the microarray and subject to sufficient conditions and time for target molecules to selectively pair with the complimentary labeled probe molecules. The microarray can be evaluated a second time to detect the level of label expressed within each quadrant after exposure to the sample.

Where the level of label expressed during the second evaluation is less that expressed during the first evaluation, at least some amount of a target molecule can be inferred to have been present in the sample, as it is the target/probe pairing which quenches the label from being detected. Further, the amount of quenching is proportionate to the amount of target molecule within the volume of the sample. Where the amount of probe molecule contained in any quadrant is known, and where the label is substantially undetectable, or detectable at baseline levels after exposure to the sample; one may infer that the sample had at least the same number of target molecules present as probe molecules on the quadrant, where pairing occurs at a 1:1 ratio of probe molecules to target molecules.

In another method of using the invention, differential gene expression profiles can be analyzed. For example, the mRNA profile or protein profile of a native cell can be compared with cells which are exposed to a treatment, for example. It is known that the expression profile for mRNA or protein or binding ability between a target and probe molecule may be radically changed due to exposure to a treatment, however, the individual molecules that are effected and the degree to which they are effected is unknown. Thus, a microarray using the labeled probe molecules of the present invention can be utilized to determine the changes in the expression profile or binding of several target molecules in a particular cell sample.

Those skilled in the art will recognize a wide range of different uses for the microarrays of the present invention. Those uses are related, in part, to those taught by others using conventional arrays such as those disclosed in U.S. Pat. Nos. 5,800,992 and 5,925,525 to Fodor, et al. For example, the arrays can be put to a variety of uses including detecting the presence of particular sequences in a given sample, and further determining differences and similarities between the probe sequences on the array and target sequences in the liquid sample, as described in U.S. Pat. No. 5,925,525 to Fodor, et al., herein incorporated by reference.

Method of Quantifying Changes in Target Molecule Expression or Function

In another method of using the invention, the number of target sequences within a cellular sample can be quantified. Specifically, beads are produced having a known number of probe molecules attached thereto. The amount of marker detected on the probe molecules of a first bead, for example fluorescence, is measured a first time. The first bead is then incubated with a sample having target molecules under time and conditions sufficient to maximize the formation of complimentary probe/target pairs. The bead is then removed from the sample, using magnetic energy when the beads include a ferromagnetic core, for example. The amount of marker detected on the first bead is measured a second time.

Where the amount of marker detected on the first bead is substantially reduced, such that it approaches zero or background measurements (the measurement of the marker on a bead not having probe molecules attached thereto, or having unlabeled probe molecules attached thereto), the first bead is discarded and a second bead is incubated with the sample having the remainder of the target molecules. Where the amount of marker detected on the second bead is substantially reduced, the second bead is discarded and the process is repeated using subsequent beads, which are incubated with the cellular sample such that substantially all of the target molecules are removed from the sample and paired onto the probe molecules of the beads. Thus, individual beads are then sequentially added to the cellular sample until the cellular sample no longer quenches the fluorescence of the beads being added. As the number of probe molecules on each bead are known, it is possible to calculate the number of target molecules which were present in the sample per volume which paired with the probe molecules and thereby, quenched the label signal. Further, where the number of target molecules present in a native cellular sample is quantified and the number of target molecules present in an experimental (in vitro or in vivo exposed to a treatment, for example) sample is quantified, the difference between these two numbers is a quantification of the effect of exposing a cell or tissue to the selected treatment conditions.

While the present invention has been described with reference to the specific embodiments thereof, it should be understood by those skilled in the art that various changes or uses may be made and equivalents may be substituted without departing from the true spirit and scope of the invention.

In addition, many modifications may be made to adapt a particular situation, material, composition of matter, process, process step or steps, to the objective, spirit and scope of the present invention. All such modifications are intended to be within the scope of the claims appended hereto. It should be noted that any of the claims below may be combined to form or practice the present invention.

What is claimed is:

1. A method for quantifying the amount of a target molecule in solution comprising the steps of:
    a. incorporating one or more fluorescing nucleotide analogs into nucleotide probes to provide fluorescing nucleotide probes;
    b. providing a first substrate having a surface area;
    c. affixing a known number of said fluorescing nucleotide probes onto the substrate;
    d. detecting a first level of fluorescence from said fluorescing nucleotide probes on the substrate;
    e. contacting said first substrate with a sample solution comprising unlabeled target nucleotide sequences;
    f. providing sufficient conditions and time for unlabeled target molecules to selectively hybridize with fluorescing nucleotide probes on said substrate wherein hybridization of an unlabeled target molecule and an fluorescing nucleotide probe quenches fluorescence from said fluorescing nucleotide probe;
    g. removing the first substrate and detecting a second level of fluorescence from said fluorescing nucleotide probes after hybridization;
    h. repeating steps a. through g with subsequent substrates, having surface areas comprising known numbers of fluorescing nucleotide probes until all target molecules are hybridized and no longer quench said fluorescing nucleotide probes; and
    i. quantifying the amount of target molecule in the sample solution by adding the known number of fluorescing nucleotide probes present on the first substrate and subsequent substrates contacted with and quenched by the unlabeled target molecule whereby the amount of the target molecule is quantified.

2. The method of claim 1, wherein said fluorescing nucleotide probes are comprised of native and nonnative nucleotides.

3. The method of claim 1, wherein the fluorescing nucleotide analogs are nucleotide analogs, including 2-amino purine for adenosine or quanine; ribonucleoside or 2,6-diamino ribonucleoside, formycin A, formycin B, oxyformycin B, toyocamycin, sangivamycin, pseudoouridine, showdomycin, minimycin, pyrazomycin, 5-amino-formycin A, 5-amino-formycin B or 5-oxo-formycin A for adenosine; 4-amino-pyrazolo [3,4d] pyrimidine, 4,6-diamino-pyrazolo [3,4d] pyrimidine, 4-oxo-pyrazolo [3,4d] pyrimidine; 4-oxo-6-amino-pyrazolo [3,4d] pyrimidine, 4,6-dioxo-pyrazolo [3,4d] pyrimidine, pyrazolo [3,4d] pyrimidine, 6-amino-pyrazolo [3,4d] pyrimidine or 6-oxo-pyrazolo [3,4d] pyrimidine for cytosine or thymidine.

4. The method of claim 1, wherein said one or more fluorescing nucleotide analogs fluoresces at a wavelength of about 300 nm to about 700 nm.

5. The method of claim 1, wherein said fluorescing nucleotide probes are further comprised of amino acids.

6. The method of claim 1, wherein said surface area has from about 100 to about 10,000 different fluorescing nucleotide probe molecules.

7. The method of claim 1, wherein the substrate is a bead.

8. The method of claim 7, wherein said bead size ranges from about 10 microns to about 20 microns.

9. The method of claim 7, wherein the bead is formed of a ferromagnetic metal core and a polymeric coating.

10. The method of claim 7, having from about 100 to about 1,000 labeled fluorescing nucleotide probe molecules attached to the surface area of the bead.

11. The method for quantifying the amount of a target molecule in a sample solution comprising the steps of:
    a. incorporating a nucleotide analog including 2-auminopurine into nucleotide probes to provide fluorescing nucleotide probes;
    b. affixing a known number of said the fluorescing probes onto a substrate;
    c. detecting a first level of fluorescence from said fluorescing nucleotide probes on the substrate;
    d. contacting said substrate with said sample solution containing unlabeled target molecules;
    e. providing sufficient conditions and time for unlabeled target molecules in said solution to selectively pair and hybridize with said fluorescing nucleotide probes affixed on said substrate wherein hybridization of an unlabeled target molecule and fluorescing probe quenches fluorescence of the nucleotide probes;
    f. removing said substrate from the solution and detecting a second level of fluorescence from the fluorescing nucleotide probes on the substrate;
    g. comparing said first and second level of fluorescence;
    h. repeating steps d. though g. by re-contacting said sample solution with said substrate or additional substrates having a known number of fluorescing nucleotide probes until target molecules no longer quench the fluorescence from said fluorescing probes; and
    i. quantifying the amount of target molecules by determining the number of quenched fluorescing probes.

12. The method of claim 11, wherein said fluorescing nucleotide probes are comprised of native and nonnative nucleotides.

13. The method of claim 11, wherein the fluorescing nucleotide probe molecules am comprised of amino acids.

14. The method of claim 11, wherein the substrate is a bead.

15. The method of claim 14, wherein said bead size ranges from about 10 microns to about 20 microns.

16. The method of claim 14, wherein the bead is formed of a ferromagnetic metal core and a polymeric coating.

17. The method of claim 14, having from about 100 to about 1,000 fluorescing nucleotide probe molecules attached to the surface area of the bead.

18. The method of claim 14, wherein the level of label expression is evaluated using a flow cytometer.

19. The method of claim 14, wherein the second level is significantly lower than the first level and said second levels of fluorescence approach zero and/or about background levels.

* * * * *

UNITED STATES PATENT AND TRADEMARK OFFICE
CERTIFICATE OF CORRECTION

PATENT NO. : 6,811,973 B1
DATED : November 2, 2004
INVENTOR(S) : Norbert Reich

It is certified that error appears in the above-identified patent and that said Letters Patent is hereby corrected as shown below:

Column 1,
Between lines 11 and 12, please insert the following.
-- STATEMENT REGARDING FEDERALLY SPONSORED RESEARCH OR DEVELOPMENT This invention was made with Government support under Grant No. MCB-9603567, awarded by the National Science Foundation. The Government has certain rights in this invention. --

Signed and Sealed this

Seventeenth Day of May, 2005

JON W. DUDAS
*Director of the United States Patent and Trademark Office*